United States Patent [19]

Maly

[11] 4,402,407
[45] Sep. 6, 1983

[54] STERILIZATION CHEST

[76] Inventor: George P. Maly, Plaza 215, 2008 Deerpark Dr., Fullerton, Calif. 92631

[21] Appl. No.: 217,176

[22] Filed: Dec. 16, 1980

[51] Int. Cl.³ .............................................. B65D 81/20
[52] U.S. Cl. .................................. 206/438; 206/363; 206/524.8; 220/209; 220/366; 422/300; 426/118
[58] Field of Search ................ 422/300; 206/363, 370, 206/438, 439, 557, 828, 524.8; 220/208, 209, 231, 306, 352, 354, 366; 426/113, 118; 229/43, 2.5 R

[56] References Cited

U.S. PATENT DOCUMENTS

| | | | |
|---|---|---|---|
| 2,181,150 | 11/1939 | Pittenger | 220/72 X |
| 3,047,177 | 7/1962 | Potrias et al. | 215/260 |
| 3,108,710 | 10/1963 | Lange et al. | 220/72 X |
| 3,357,593 | 12/1967 | Sears, Jr. et al. | 220/72 |
| 3,463,378 | 8/1969 | Daalen | 229/2.5 R X |
| 3,480,878 | 11/1969 | Morgan | 229/2.5 R X |
| 3,521,808 | 7/1970 | Weiss | 229/2.5 R X |
| 3,697,223 | 10/1972 | Kovalcik et al. | 206/370 |
| 3,707,227 | 12/1972 | Britt | 229/2.5 R X |
| 4,058,214 | 11/1977 | Mancuso | 229/2.5 R X |
| 4,117,950 | 10/1978 | Allen | 229/43 X |
| 4,124,141 | 11/1978 | Armentrout et al. | 229/43 X |
| 4,149,650 | 4/1979 | Whelchel et al. | 220/231 X |
| 4,247,517 | 1/1981 | Sanderson et al. | 220/208 X |

FOREIGN PATENT DOCUMENTS 1187991 2/1965 Fed. Rep. of Germany ...... 220/366

Primary Examiner—William Price
Assistant Examiner—Gary E. Elkins
Attorney, Agent, or Firm—Fischer, Tachner & Strauss

[57] ABSTRACT

There is disclosed a container that is useful as a sterilization chest for surgeons' instruments and the like. The container includes a generally open-top box having a peripheral flange about its top edge and an open channel extending along at least two of the opposite sides of the box in the peripheral flange. A flexible membrane cover is provided which overlies the top of the box and the peripheral flange and this membrane is reinforced with a plurality of stiffening members which are supported on the undersurface of the flexible membrane cover in a side-to-side array. These stiffening members have distal, downwardly dependent lips which are received in the open channel grooves in the peripheral flange whereby the stiffening members reinforce both the flexible cover and the upper sidewalls of the box, preventing collapse of these elements when the chamber within the chest is evacuated. The flexible cover serves to seal the container yet it can be readily removed by lifting from a corner and, in this fashion, also serves as a valve for the sterilization chest.

11 Claims, 3 Drawing Figures

STERILIZATION CHEST

BACKGROUND OF THE INVENTION

This invention relates to a sealable container and in particular, to a container useful as a sterilization chest.

Sterilization chests which have been used heretofore have been generally hemispherically shaped containers having a domed closure member and a check valve which can be manually opened. Typically, the instruments are placed in the chest and the chest is placed in an autoclave and subjected therein to a heating and cooling cycle for thermal sterilization of the instruments. When the chest is removed from the autoclave, it remains under vacuum until the valve is opened, preparatory to use of the instruments. A common failing of these prior steam chests is the malfunctioning of the manual valve from rust and mechanical wear, resulting in loss of the vacuum seal and requiring frequent and increasing need for repeated autoclaving.

BRIEF DESCRIPTION OF THE INVENTION

This invention comprises a simple and improved container useful as a sterilization chest. Although the chest is ideally suited for medical instruments it also has other uses. The sterilization chest is formed of an open top container, such as a box which has a peripheral flange about is upper edges. An open channel groove is provided in the top surface of this flange along at least two opposite sides of the container. A flexible membrane cover which overlies the top of the container and the peripheral flange is provided and a plurality of stiffening members are carried on the undersurface of this flexible membrane cover, disposed in a side-to-side array thereon. The stiffening members have distal downwardly dependent legs which are received in the open channel grooves whereby the stiffening members serve to reinforce the flexible membrane cover as well as the upper side walls of the container, which are thus held together and restrained from bending or buckling when the container is under a vacuum.

Preferably, the side walls and bottom of the container are reinforced with stiffening ribs, permitting the container, when closed and sealed, to withstand a differential pressure of at least one atmosphere. The flexible membrane cover serves as the sealable cover and as the valve to release the internal vacuum of the container since this membrane is flexible and can be peeled from a corner when it is desired to open the container.

BRIEF DESCRIPTION OF THE DRAWINGS

The invention will be described with reference to the Figures of which.

DESCRIPTION OF PREFERRED EMBODIMENTS

Figure 1:
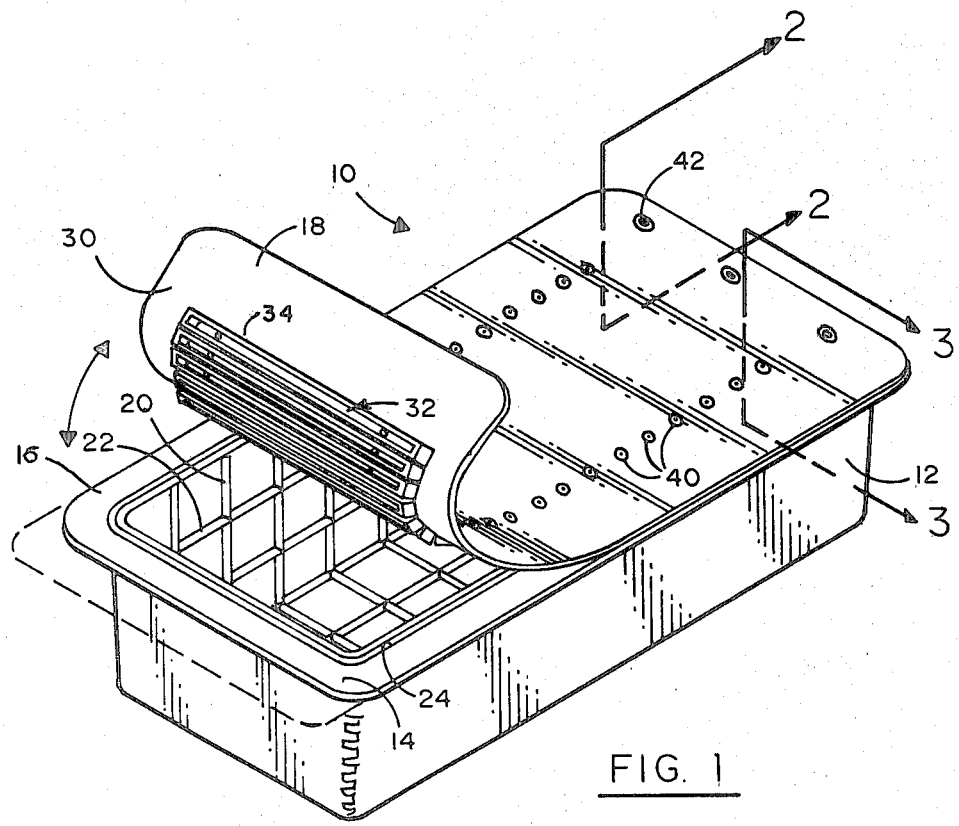
FIG. 1 is a perspective view of the invention showing the cover in a partially open position.

Referring now to FIG. 1, the sterilization chest 10 comprises an open top box 12 having a peripheral flange 14 about its upper edge. Flange 14 is of sufficient annular width to provide a sealing surface 16 for engagement by the flexible membrane cover 18. The latter overlies the open top of the box and the peripheral flange 14.

Preferably, box 12 is formed of injection molded plastics, however, glass, pressed sheet metal and the like can also be used. Preferably transparent materials such as transparent plastics or glass are used to permit viewing the contents without the necessity to open the chest. The box 12 is formed with integral reinforcement such as the transverse ribs 20 and longitudinal ribs 22 in the bottom and sides which are molded into the shaped material forming these walls, thereby stiffening and reinforcing the construction.

An open channel groove 24 is provided in the peripheral flange 14. This groove is coextensive with at least two opposite sides of the box 12, and preferably extends entirely about the periphery of the box substantially as shown.

The flexible membrane cover 18 carries, on its undersurface 30, a plurality of stiffening members 32. The latter are narrow bars which are disposed in side-to-side array across the undersurface of flexible membrane 18. To provide enhanced stiffness, these bars can be formed with a longitudinal web 34 (see also FIG. 2) coextensive with their length. The stiffening members 32 can be formed of any suitable material such as metal, plastic and the like. A very suitable material is polyphenylene sulfide which is a crystalline aromatic polymer having a high thermal stability and excellent corrosion resistance. Other suitable plastics include polycarbonates, polyimides, and fluoroplastics. A suitable construction comprises extruded plastic in the form of an angle or channel member. At their opposite ends, the stiffening members have downwardly dependent legs 36 which are received in the open channel groove 24. The stiffening members can be secured to the undersurface of flexible membrane by adhesive bonding and/or by fasteners such as rivets 40.

The flexible member cover can be secured at one end to the peripheral flange 16 by a plurality of fasteners such as rivets 42. Additionaly, a preferred construction provides a membrane cover 16 which is slightly longer than the peripheral flange 16 to provide a grasping area shown in phantom lines on FIG. 1 that will permit a user to grasp the flexible membrane cover when attempting to lift or peel the cover from its seal about the peripheral flange.

Figure 2:
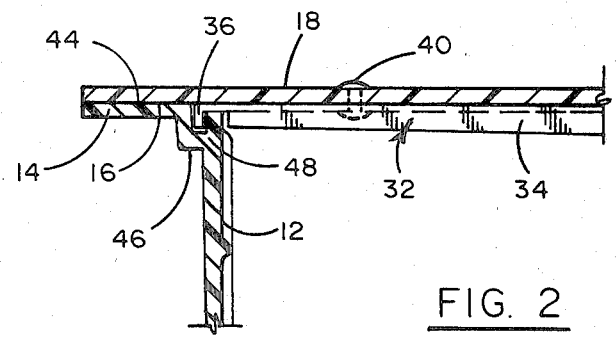
FIG. 2 is a partial sectional view along lines 2—2 of FIG. 1.

Referring now to FIG. 2, there is illustrated a partial sectional view along lines 2—2 of FIG. 1. As illustrated, the flexible membrane cover 18 rests upon the peripheral flange 14 and is sealably engaged therewith along the interface line 44. The stiffening members 20 are shown with distal downwardly dependent legs 36 which are received within the open channel groove 24 which is provided in rim 46 that peripherally surrounds the upper edge 48 of the side walls of the box 12. The reinforcement web 34 is also shown in this illustration and, preferably, this reinforcement web increases in width towards its center.

Figure 3:
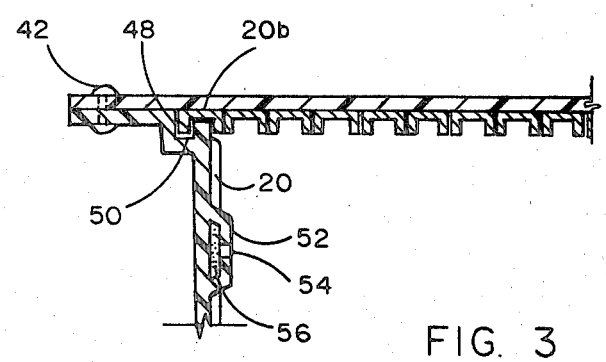
FIG. 3 is a partial sectional view along lines 3—3 of FIG. 1.

In a preferred embodiment, moisture sensitive and indicating means can also be included in the assembly. This is shown in FIG. 3 as pocket 52 formed on the inside wall of the box 12. The pocket 52 is provided with one or more apertures 54 to provide communication with the interior of the box and a moisture sensitive indicator, e.g., a water sensitive salt 56, is placed within the pocket. These salts exhibit a color change with a change in moisture content, thereby indicating to the user the humidity condition of the interior of the box.

As shown in FIG. 3, the last transverse stiffening rib 20b has its outermost web 48 received within the transverse portion 50 of the open channel groove 24.

The box 12 can be formed of any suitable materials which retain their strength and shape at temperatures up to about 350 degrees Fahrenheit, the maximum temperature experienced in the steam sterilization of utensils. Suitable plastics which can be used for such service include plastics such as furan resins, phenolic resins and Novolacs, thermosetting resins; or thermoplastics such as polyimides, polyphenylene sulfide, Teflon, phenolic resins, Kel-F; all alone, or reinforced, as well as metals such as stainless steel, aluminum and other corrosion resistant metals. Suitable reinforcing materials can be chopped or long fibers of glass, carbon, graphite, boron, etc., as well as pyrolytic silica of a size from 0.003 to about 0.015 micron diameter, hollow or solid glass particles or spheres of distributed sizes from 0.001 to about 0.050 inch. If desired, the box can also be formed of glass. When the box is formed of plastics it is preferably injection molded and, for this purpose, the sidewalls are provided with a slight draft to facilitate ejection from the fabrication mold.

The flexible membrane cover can be formed of any suitable temperature resistant plastic such as synthetic rubber, fluorocarbon rubber, Viton, or preferably, silicon rubber. This material should be flexible and impermeable to air and should be fabricated with a sufficiently high surface finish as to provide an airtight seal along the interface line 44 when the interface line 44 when the interior of the chest is evacuated.

The stiffening members 20 can be formed of any plastic having a high strength at temperatures of about 350 degrees F. Fiber reinforced plastics can be used, e.g., any of the aforementioned plastics can be used with up to about 40 percent or more of a fiber reinforcement such as fiberglass, carbon or graphite fibers, etc. The stiffening members can also be formed of metal such as stainless steel, aluminum, brass, bronze, nickel alloys, etc. The stiffening members can be formed of stamped or injection molded items, or an extrusion such as an an extruded channel cut to the necessary length and machined at each end to provide the downwardly dependent legs which are received within the open channel groove of the box 12.

In use, the medical instruments are loaded into the box 12, the cover 18 is closed and the box is placed in an autoclave and subjected therein to temperatures of about 225 to 350 degrees F. at subatmospheric pressures for sufficient time to effect sterilization of the box contents. The flexible cover lifts and readily permits evacuation of the interior of the box. The autoclave typically is operated with a heating and a cooling cycle. When the box is withdrawn from the steam chamber its interior is at a vacuum and the flexible membrane cover is compressed by the surrounding atmosphere against flange 14 and thus sealably engages with the flange 14, preventing entrance of the air and insuring that the interior of the box remains at a vacuum. The flexible membrane readiliy exhibits the evacuated and sealed condition of the box since it deflects inwardly slightly between the adjacent stiffening members. Users can, thus determine at a glance whether or not the box remains sealed and its contents sterile. The seal of the box is also apparent when it is opened, since the sealed box will give off an air-rushing sound when opened.

The user can readily extract the contents from the box 12 simply by grasping the end flat of flexible membrane 18 and lifting the membrane to peel it from its sealed engagement with the peripheral flange to open the container. Thereafter, the flexible membrane cover can be replaced on the flange, however, it will not reseal to the flange until the sterization procedure is repeated.

The stiffening members key into the groove about the sidewalls of the box, thereby preventing the sidewalls from collapsing under the greater external pressure. The stiffening members provide reinforcement for the flexible membrane cover 18, preventing an inward collapse of this member.

The invention has been described with reference to the illustrated and presently preferred embodiment. It is not intended that the invention be unduly limited by this description of preferred embodiments. Instead, it is intended that the invention be defined by the means, and their obvious equivalents, set forth in the following claims.

I claim:

1. A container which seals upon evacuation comprises:
    (a) an open-top receptacle having upright sidewalls and a bottom wall;
    (b) a peripheral flange about the upper edges of its sidewalls of sufficient width to provide an annular, flat sealing surface;
    (c) open channel grooves in said flange, one each, extending along each of at least two opposite sides of said receptacle and located inwardly on said flange surrounded by said annular, flat sealing surface;
    (d) a flexible membrane cover overlying said open top with outside sealing face edges overlying said annular flat sealing surface of said peripheral flange and in sealed contact with said annular flat sealing surface when said chamber is evacuated;
    (e) a plurality of membrane stiffening members in side-to-side array carried on the underside of said flexible membrane and terminating short of the sealing face edges with distal legs received in each of said grooves.

2. The container of claim 1 including stiffening ribs in said sidewalls.

3. The container of claim 2 including stiffening ribs in said bottom wall.

4. The container of claim 3 wherein said stiffening ribs extend longitudinally and laterally in a waffle pattern.

5. The container of claim 4 wherein said stiffening ribs are integral with said container walls and line the inside surfaces thereof.

6. The container of claim 1 wherein said membrane stiffening members are crossbars extending laterally across the undersurface of said membrane.

7. The container of claim 6 wherein said crossbars are channel members.

8. The container of claim 1 including at least one membrane grasping area extending past the outer edge of said flange to permit lifting of said membrane and opening of said container.

9. The container of claim 1 wherein said channel grooves in said flange extend longitudinally along each sidewall of said receptacle and said membrane stiffening members extend laterally across the undersurface of said membrane with their distal legs seated in each of said grooves.

10. The container of claim 1 formed of transparent plastic.

11. The container of claim 1 wherein said receptacle is a rectangularly shaped box.

* * * * *